United States Patent [19]

Smith

[11] Patent Number: 5,588,423

[45] Date of Patent: Dec. 31, 1996

[54] HUMIDIFIER CHAMBER

[75] Inventor: Malcolm D. Smith, Auckland, New Zealand

[73] Assignee: Fisher & Paykel Limited, Auckland, New Zealand

[21] Appl. No.: 529,523

[22] Filed: Sep. 18, 1995

[30] Foreign Application Priority Data

Aug. 20, 1994 [NZ] New Zealand .................. 264485

[51] Int. Cl.$^6$ .................................................. A61M 16/16
[52] U.S. Cl. ................... 128/203.26; 128/203.17; 128/204.14
[58] Field of Search .................. 128/203.12, 203.17, 128/204.17, 203.26, 203.27, 204.14; 261/119.1, 142, DIG. 65

[56] References Cited

U.S. PATENT DOCUMENTS

| 670,084 | 3/1901 | Sloane | 128/203.26 |
|---|---|---|---|
| 3,193,261 | 6/1965 | Nesbitt | 261/142 |
| 3,219,795 | 11/1965 | Wiseman | 261/142 |
| 3,610,879 | 10/1971 | Katzman | 128/203.17 |
| 3,638,926 | 2/1972 | Melville et al. | 261/142 |
| 3,971,913 | 7/1976 | Myklebust | 128/203.27 X |
| 4,621,632 | 11/1986 | Bartels et al. | 128/203.27 |
| 5,195,514 | 3/1993 | Liu et al. | 128/203.17 |

FOREIGN PATENT DOCUMENTS

| 143463 | 5/1935 | Austria | 128/203.26 |
|---|---|---|---|
| 0127368 | 12/1984 | European Pat. Off. | 128/204.17 |
| 463253 | 2/1914 | France | 128/203.26 |
| 2591490 | 6/1987 | France | 128/203.17 |
| 535678 | 10/1931 | Germany | 128/203.26 |
| 257247 | 9/1948 | Switzerland | 128/203.27 |
| 615698 | 1/1949 | United Kingdom | 128/204.14 |

*Primary Examiner*—V. Millin
*Assistant Examiner*—Eric P. Raciti
*Attorney, Agent, or Firm*—Trexler, Bushnell, Giangiorgi & Blackstone, Ltd.

[57] ABSTRACT

A humdification chamber for the humidification of respiratory gases has particular application for use over extended time periods with infrequent refills.

The humidification chamber has a heated reservoir and a supply reservoir, the heated reservoir adapted to be in thermal contact with a heater base to which the humidification chamber is attached. A partition separates the heated reservoir from the supply reservoir, the partition having a gas flow path and a liquid flow path, the flow paths allowing gas and liquid communication respectively between the supply and heated reservoirs. The partition substantially thermally insulates the supply reservoir from the heater base. A gas inlet port and a gas outlet port are provided in the top surface of the humidification chamber to allow gases to be humidified to circulate through the chamber above the heated reservoir.

In use the humidifier chamber has a large overall liquid capacity and therefore a longer duration between refills is available, while the heater base is required to heat substantially only the heated reservoir. The extended use chamber may be used with existing heater bases.

12 Claims, 1 Drawing Sheet

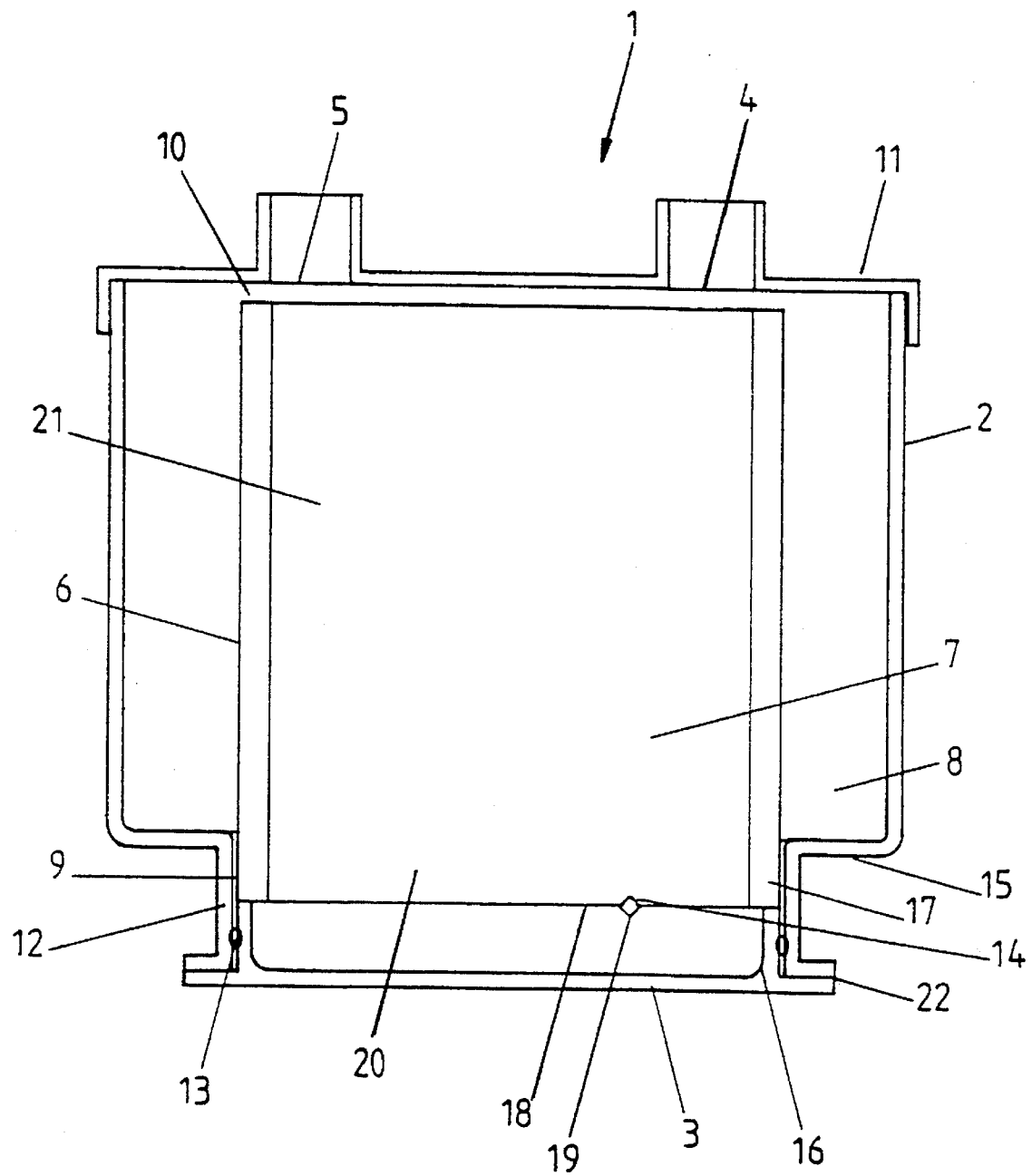

HUMIDIFIER CHAMBER

BACKGROUND TO THE INVENTION (1) Field of the Invention

This invention relates to humidifier chambers for use with heated humidifier bases, in the humidification of gases for respiratory breathing circuits.

(2) Description of the Prior Art

It is well known to humidify the gases in a respiratory breathing circuit to reduce the discomfort to a patient. Humidifiers are known having a heated element, to heat a reservoir of water present in a chamber placed on the element, with gases passed from a ventilator into the chamber whereupon the gases absorb water vapour generated by the heating process, the gases then exiting the chamber in a state of substantially increased humidity. Due to this process the water level in the chamber drops over time. In many situations this is not important, as for example in a hospital, hospital staff can regularly check the water level in the chamber, and when required may add water to the chamber. However, the use of such humidification devices has also become more prevalent in the home and in facilities where it is inconvenient for round-the-clock monitoring of the water level. Therefore it is necessary that enough water is available to the humidification chamber to humidify the gases for a considerable period of time, for example up to eight hours. A number of methods are known for doing this, for example water may be supplied to the chamber from a water bag through a regulated water supply. Systems such as this are inherently expensive and require specialised supplies.

Another alternative is a humidification chamber which supplies water to a compartment adjacent the heater element by a siphonic system. This apparatus has the disadvantage that to operate successfully the humidification chamber must be and remain airtight, and is difficult to thoroughly clean in a household situation.

BRIEF SUMMARY OF THE INVENTION

Therefore it is an object of the present invention to provide a respiratory humidification chamber that will at least go some way towards overcoming the above disadvantages.

Accordingly the invention consists in a respiratory humidifier chamber for attachment to a heater base, said chamber comprising a closed watertight vessel having a heat conductive base, said vessel having a gases inlet for receiving gases from a ventilator and a gases outlet for delivering humidified gases to a patient, a thermal insulating partition inside said vessel dividing said vessel into a first heated reservoir, and a second supply reservoir, said first reservoir defined by at least said partition and a first portion of said vessel, said first portion including said heat conductive base, said second reservoir defined by at least said partition and a second portion of said vessel, said second portion not including said heat conductive base, and at least one gases communication path between said first and second reservoirs at or adjacent the top of said partition.

The invention consists in the foregoing and also envisages constructions of which the following gives examples.

BRIEF DESCRIPTION OF THE DRAWING

One preferred form of the present invention will now be described with reference to the accompanying drawing which shows a cross-sectional side elevation of a respiratory humidification chamber.

DETAILED DESCRIPTION

With reference to the drawing, a humidification chamber 1 for connection to a heater base such as a Fisher & Paykel MR410 heater base is shown. The humidification chamber 1 is formed as a closed watertight vessel 2 with a heat conductive base 3, for conducting heat from the heater base to liquid placed in the humidification chamber 1. An outwardly extending flange 22 is provided around the base 3 for mounting the chamber 1 on a heater base. The humidification chamber is intended to be an element in a respiratory breathing circuit, and has a gases inlet 4 for receiving gases from a ventilator, and a gases outlet 5 for delivering humidified gases to a patient. The gases inlet 4 and the gases outer 5 are preferably formed as a protruding port so that breathing circuit hoses may be attached thereto.

For extended periods of use, it is proposed that a larger chamber than would normally be the case be used for accommodating a larger amount of liquid. However, simply increasing the volume of liquid in the humidification chamber increases the heat output requirement of the heater base, and therefore such a chamber will not work optimally on standard heater bases. Therefore in the present invention, the preferred embodiment of which is shown in the accompanying drawing, the body of liquid in humidification chamber 1 is separated into a first heated reservoir 7 and a second supply reservoir 8, separated by a thermal insulating partition 6. The first heated reservoir 7 is adjacent and in contact with the heat conductive base 3 and accepts heat therefrom, while the supply reservoir 8 is thermally insulated from the heated reservoir 7 and the heat conductive base 3 by the thermal insulating partition 6. Therefore with the apparatus of the present invention, only the liquid in heated reservoir 7 is heated directly by the heater base and the liquid in supply reservoir 8 is not directly heated by the heater base. The liquid in the supply reservoir 8 receives only limited heating by conduction through the thermally insulating partition 6, and by limited convection through fluid flow between the supply reservoir 8 and the heated reservoir 7.

Therefore the liquid in the supply reservoir 8 is maintained at a lower temperature than the heated reservoir 7, and the heat loss through the exterior wall of the vessel 2 is lower than if the entire water supply were maintained at the temperature of the heated reservoir 7. Consequently the load on the heater base is reduced to levels achievable by standard heater bases.

Heating of the heated reservoir 7 causes liquid vapour to emanate from the liquid for humidification of the air passing through the chamber from gases inlet 4 to gases outlet 5. This process consumes liquid from the heated reservoir 7. In the present invention water is supplied to first heated reservoir 7 from second supply reservoir 8 as water is used from first heated reservoir 7, through a liquid communication path 9 flowing down through the vertical channel between the partition 6 and the wall of the vessel 2, and thence under the bottom edge of the partition 6. Preferably the liquid communication path 9 is sufficient to allow a supply of liquid to flow from supply reservoir 8 to heated reservoir 7, while also being sufficiently constrained to substantially eliminate convective currents flowing between reservoirs 7 and 8, which would otherwise reduce the effectiveness of the thermal insulating partition 6. Constraining the liquid flow path therefore reduces the transfer of heat from reservoir 7 to reservoir 8.

A gases communication path 10 is also provided to allow the liquid level in first heated reservoir 7 and second supply reservoir 8 to equalise. This ensures that water present in second supply reservoir 8 can flow into the first heated reservoir 7 without the possibility of cessation of flow due to the creation of a vacuum in the supply reservoir 8. In the preferred form of the invention shown in the drawing, thermal insulating partition 6 is a cylindrical wall approximately at the circumference of the heat conductive base 3, the cylindrical wall forming a substantial thermal barrier between heated reservoir 7 and supply reservoir 8. The cylindrical wall is made of a material having reasonable insulating properties, for example PLEXIGLAS.

It is advantageous for the present invention that the humidification chamber 1 is capable of disassembly, for example for the purposes of cleaning. Therefore in the preferred form of the invention the heat conductive base 3 is removable from the chamber 1 and the thermal insulating partition 6 is removable through the created opening. To ensure that the chamber is watertight with the heated conductive base 3 in place, a seal 13 is provided between the heat conductive base 3 and the vessel 2. Alternatively, the humidification chamber 1 may be provided with a removable lid 11, and removing the lid allows the thermal insulating partition 6 to be passed through the created opening.

In the preferred form of the invention the thermal insulating partition 6 is centrally located in the chamber, about the circumference of heat conductive base 3, and it is therefore necessary to maintain the insulating partition 6 in this position. Therefore locating means 12 are provided to locate the insulating partition 6. Locating means 12 could, as in the preferred form of the invention shown in the drawing, be an annular ledge in the humidification chamber, inside or outside which the partition is located. This has the added advantage of providing a tortuous fluid flow path to thereby reduce the convection between reservoirs 7 and 8.

In the preferred form of the invention as shown in the drawing, the insulating partition 6 is loosely fitted within the humidification chamber 1 and loosely located by locating means 12, so that liquid communication path 9 is effectively provided by the loose tolerances between the insulating partition 6 and the locating means 12, and gases communication path 10 is provided by the apparent space between the top edge of the thermal insulating partition 6 and the internal surface of the humidification chamber 1. Alternative forms are also envisaged, for example the insulating partition 6 might be a better fit for humidification chamber 1 and locating means 12 but have channels or apertures provided at the base of partition 6 for liquid communication and at the top edge of partition 6 for gases communication.

In the preferred embodiment of the invention the vessel wall 2 includes an outward step 15 as the wall progresses upwards from the base 3. A portion 20 of the vessel 2 below the step 15 is thereby defined which has a lesser internal diameter than the portion 21 which is above the step 15. At least the bottom portion of the insulating partition 6 has an outside diameter which is slightly less than the inside diameter of the portion 20 of the vessel 2 which is below the outward step 15. The bottom portion of the insulating partition 6 is located in the portion 20 of said vessel of lesser internal diameter, located in its position by the annular ledge 12 formed by outward step 15.

In the form of the invention shown the lower edge 17 of partition 6 rests on the top edge 18 of an annular ring 16 which depends upwardly from the heat conductive base 3. The upwardly dependant annular ring 16 locates the heat conductive base 3 onto the vessel 2, with seal 13 provided between the annular ring 16 and the annular ledge 12 to ensure a watertight connection.

With partition 6 resting on the annular ring 16, water flow path 9 is provided by the seepage through the abutment of the bottom edge of the partition 6 and the top edge of the annular ring 16. However to ensure an adequate flow is provided even with low fluid levels in the supply reservoir 8, a situation having low potential head between the supply and heated reservoirs, it may be necessary to include one or more grooves 14, 19 in either the bottom edge of partition 6 or the top edge of annular ring 16. It is preferable that if such grooves are to be provided only one groove be provided so that a convective flow pattern is not set up with fluid entering the heated reservoir 7 through one groove and exiting through another. With only one groove a positive flow from supply reservoir 8 into heated reservoir 7 will be conveniently maintained by the extraction of fluid from heated reservoir 7 by the humidification of gases flowing through the chamber. Such a configuration has reduced potential for convective heating of the supply reservoir 8.

The insulating partition 6 is preferably of sufficient height that when positioned with its bottom end within the area of lesser internal diameter, the length of overlap into the area of lesser internal diameter is greater than the distance between the top edge of the partition 6 and the lid portion 11 of the vessel 2. This ensures that once the humidifier chamber has been assembled, for example after cleaning, the partition, while still only loosely fitted, may not fall out of position.

In use the humidification chamber 1 is filled with water to a given level, which can for example be marked on the exterior of the humidification chamber, through the gases inlet 4 or gases outlet 5, and the level in supply reservoir 8 shortly equalises with the level in heated reservoir 7. Gases conduit from the respiratory ventilator is then connected to gases inlet port 4 and further conduit is provided between gases outlet 5 and the patient. Gases passing through the chamber are humidified by the water vapour generated through the heating of heated reservoir 7, and the level of liquid in heated reservoir 7 falls, but the water consumption is shared by supply reservoir 8. Therefore, although the heated base is required to substantially only heat the liquid in heated reservoir 7, sufficient liquid is present in the humidification chamber 1 for extended use. For example a chamber constructed according to the present invention may contain sufficient water for up to eight hours' use between refills, but still be suitable for attachment to standard heater bases such as the Fisher & Paykel MR410.

I claim:

1. A respiratory humidifier chamber for attachment to a heater base, said chamber comprising:

a closed watertight vessel having a heat conductive base, said vessel having a gases inlet for receiving gases from a ventilator and a gases outlet for delivering humidified gases to a patient, a thermal insulating partition inside said vessel dividing said vessel into a first heated reservoir, and a second supply reservoir, said first reservoir defined by at least said partition and a first portion of said vessel, said first portion including said heat conductive base, said second reservoir defined by at least said partition and a second portion of said vessel, said second portion not including said heat conductive base, at least one liquid communication path between said first and second reservoirs at or adjacent the bottom of said partition, and at least one gases communication path between said first and second reservoirs at or adjacent the top of said partition.

2. A respiratory humidifier chamber as claimed in claim 1 wherein said vessel base is removable to allow said partition to be removed from said vessel.

3. A respiratory humidifier chamber as claimed in claim 1 wherein said vessel is provided with a removable lid to allow said partition to be removed from said vessel.

4. A respiratory humidifier chamber as claimed in claim 1 wherein said vessel has a wall which is cylindrical, said insulating partition is a freely moveable hollow cylinder of substantially less diameter than said vessel wall, said vessel includes locating means to locate said partition concentrically with said vessel wall, and said hollow cylinder extends from the bottom of the vessel almost to the top of the vessel.

5. A respiratory humidifier chamber as claimed in claim 4 wherein said locating means comprises an annular ledge, and said partition is constrained from substantial horizontal movement by said annular ledge.

6. A respiratory humidifier as claimed in claim 1 wherein said liquid communication path is tortuous and is configured to in use substantially eliminate convective fluid flow between said first heated reservoir and said second supply reservoir.

7. A respiratory humidifier chamber for attachment to a heater base, said chamber comprising:

a closed watertight vessel having a heat conductive base, said vessel having a cylindrical wall, said vessel having a gases inlet for receiving gases from a ventilator and a gases outlet for delivering humidified gases to a patient, a thermal insulating partition inside said vessel dividing said vessel into a first heated reservoir, and a second supply reservoir, said first reservoir defined by at least said partition and a first portion of said vessel, said first portion including said heat conductive base, said second reservoir defined by at least said partition and a second portion of said vessel, said second portion not including said heat conductive base, said insulating partition being a freely moveable hollow cylinder of substantially less diameter than said vessel wall, said vessel includes locating means to locate said partition concentrically with said vessel wall, and said hollow cylinder extends from the bottom of the vessel almost to the top of the vessel, said vessel wall includes an outward step as said wall progresses upwards, said vessel wall below said step defining an area of said vessel of lesser internal diameter than the internal diameter of said vessel above said step, said lesser diameter being larger than the outer diameter of at least a lower portion of said insulating partition, and the lower portion of said insulating partition is located in said area of lesser internal diameter, at least one liquid communication path between said first and second reservoirs at or adjacent the bottom of said partition, and at least one gases communication path between said first and second reservoirs at or adjacent the top of said partition.

8. A respiratory humidifier chamber as claimed in claim 7 wherein the external diameter of the lower portion of said insulating wall is less than but substantially equal to the internal diameter of said area of lesser internal diameter.

9. A respiratory humidifier chamber as claimed in claim 7 wherein said removable vessel base has an upwardly depending annular ring, said ring fitting closely inside said area of lesser diameter, sealing means are disposed between said ring and said vessel wall for sealing a junction between said ring and said vessel wall, and the lower edge of said insulating partition rests on the top edge of said annular ring.

10. A respiratory humidifier chamber as claimed in claim 9 wherein at least one groove is provided in a bottom edge of said insulating partition, extending from the inner side of said bottom edge of the outer side of said bottom edge.

11. A respiratory humidifier chamber as claimed in claim 9 wherein at least one groove is provided in a top edge of said annular ring, extending from the inner side of said top edge to the outer side of said top edge.

12. A respiratory humidifier chamber as claimed in claim 7 wherein the length of overlap between said insulating partition into said area of lesser internal diameter is greater than the distance between a top edge of said partition and a top surface of said vessel.

* * * * *